United States Patent [19]

Harada et al.

[11] 4,251,643
[45] Feb. 17, 1981

[54] ABSORBENTS WITH IMPROVED WATER ABSORBING POWER

[75] Inventors: Kazuto Harada; Toshihiko Yoshitake, both of Kurashiki, Japan

[73] Assignee: Kuraray Co., Ltd., Kurashiki, Japan

[21] Appl. No.: 21,169

[22] Filed: Mar. 16, 1979

[30] Foreign Application Priority Data

Mar. 23, 1978 [JP] Japan .................. 53/34575

[51] Int. Cl.$^3$ ............................. C08F 8/46
[52] U.S. Cl. ......................... 525/51; 128/284; 128/285; 525/61
[58] Field of Search ............... 526/7; 525/59, 61; 128/284, 285

[56] References Cited

U.S. PATENT DOCUMENTS

| | | | |
|---|---|---|---|
| 2,403,112 | 7/1946 | Muskat | 260/78 |
| 2,759,909 | 8/1956 | Gordon et al. | 260/78.5 |
| 2,796,413 | 6/1957 | Baer | 260/78.4 |

FOREIGN PATENT DOCUMENTS 45-21313  7/1970  Japan .
55-21312  7/1980  Japan .
55-21314  7/1980  Japan .

*Primary Examiner*—Stanford M. Levin
*Attorney, Agent, or Firm*—Oblon, Fisher, Spivak, McClelland & Maier

[57] ABSTRACT

Absorbent materials for aqueous fluids, which absorb fluid rapidly and swell uniformly, comprise modified polyvinyl alcohol polymers obtained by reacting in an anhydrous condition a polyvinyl alcohol polymer with a cyclic acid anhydride and causing partial crosslinking of said polymer. Absorbent articles such as diapers, sanitary napkins, sanitary tampons, blood absorbents for use in surgical operations, bandages and dressings comprise said absorbent materials and fluid absorbing holders therefor.

13 Claims, 6 Drawing Figures

ABSORBENTS WITH IMPROVED WATER ABSORBING POWER

BACKGROUND OF THE INVENTION

1. Field of the Invention

This invention relates to absorbent material comprising specific modified polyvinyl alcohol type polymers and to absorbent articles comprising the same. More particularly, it relates to absorbent materials, which absorb aqueous fluids rapidly and swell uniformly, and which comprise modified polyvinyl alcohol type polymers obtained by reacting in anhydrous conditions polyvinyl alcohol type polymers with cyclic acid anhydrides and causing partial crosslinking of said polymers as well as to absorbent articles comprising said absorbent materials and fluid absorbing holders therefor, such as diapers, sanitary napkins, sanitary tampons, blood absorbents for use in surgical operations, bandages and dressings. (Hereinafter, the abbreviation "PVA" denotes "polyvinyl alcohol".)

2. Description of the Prior Art

In recent years, with the increase of the range of use of hydrophilic polymeric materials in the fields of medical industry, food industry and agriculture, water-insoluble but hydrophilic or water absorbing polymeric materials, among others, have found use as materials for separation or purification purposes and carriers for liquid chromatorgraphy, culture mediums for microbes and plants, and medical materials such as contact lenses and dressings for surgical sutures, and other various uses taking advantages of their water absorbing or holding power. Among these applications, those making the most use of water absorbing power, include the uses in the sanitary field such as diapers, sanitary napkins, sanitary tampons, blood absorbents for use in surgical operations, bandages and dressings. These uses require polymeric materials not only capable of rapidly absorbing or removing large quantities of body fluids such as urine and blood but also capable of giving to the structure of the products made therefrom a property such that the body fluids absorbed by the structure neither wet the skin nor give an unpleasant feeling.

As polymeric materials to be used for these applications, there have been proposed several materials derived from natural and synthetic polymeric materials, such as modified polyethylene oxides, crosslinked polyvinyl pyrrolidones, crosslinked sulfonated polystyrenes and saponified starch-acrylonitrile graft copolymers.

However, their water absorbing power, except for the case of the saponified starch-acrylonitrile copolymer, is weak, rendering them unsatifactory as water absorbing materials. In the case of the saponified starch-acrylonitrile graft copolymer which can absorb water in amounts more than 30 times its own weight, too, there are several problems from a practical standpoint, for example, the decay of the starch constituent may possibly lead to destruction of the gel structure. The conventional absorbent materials, such as those from pulps, which do not contain such synthetic or semi-synthetic absorbent materials as mentioned above, have disadvantages such as that, owing to their low absorbing power per unit of volume, increased volumes are required to increase absorption, raising the cost of production and making the products uncomfortable to wear.

SUMMARY OF THE INVENTION

It is therefore an object of the invention to provide absorbant materials capable of absorbing aqueous fluid rapidly and swelling uniformly.

Another object of the invention is to provide absorbing materials useful in absorbing articles such as diapers, sanitary napkins, sanitary tampons, blood absorbants for use in surgical operations, bandages, and dressings.

A further object of the invention is to provide absorbing materials capable of rapidly absorbing large quantities of body fluids and giving final products with structures that will neither wet the skin nor give unpleasant feelings.

Still another object of the invention is to provide absorbing materials which can absorb large amounts of fluids per unit weight and which will not decompose or destruct thereafter.

Still a further object of the invention is to provide absorbing materials which have high absorbing power per unit of volume.

These and other objects of the invention as will hereinafter become more readily apparent can be obtained by providing an absorbing material for aqueous fluids comprising a modified polyvinyl alcohol polymer obtained by reacting a polyvinyl alcohol polymer in anhydrous state with a cyclic acid anhydride and thereby causing partial cross-linking of said polymer.

These objects can also be attained by providing absorbant articles such as diapers, sanitary napkins, sanitary tampons, blood absorbants for use in surgical operations, bandages and dressings comprising said aforementioned absorbing materials and fluid absorbing holders therefor.

BRIEF DESCRIPTION OF THE DRAWINGS

A more complete appreciation of the invention and many of the attendant advantages thereof will be readily obtained as the same becomes better understood by reference to the following detailed description, when considered in connection with the accompanying drawings, wherein.

DETAILED DESCRIPTION OF THE PREFERRED EMBODIMENTS

Figure 1:
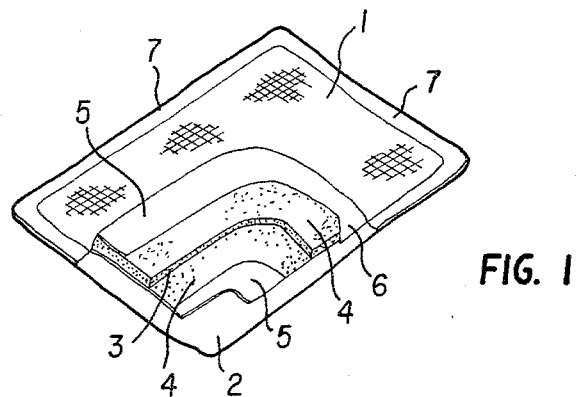
FIG. 1 is a perspective view of a diaper with a portion thereof cut off.

Intensive researches by the present inventors to develop absorbents with improved water absorbing power but without the above disadvantages have shown the modified PVA type polymer particles, obtained by reacting in anhydrous conditions a PVA type polymer with a cyclic acid anhydride and causing thereby partial crosslinking of said polymer, are substantially insoluble in water, absorb large quantities of water rapidly, and can be mass-produced at low costs, and that absorbent articles composed of fluid absorbing holders and said modified PVA type polymer particles dispersed and packed therein have excellent water absorbing power and show rapid rates of water absorption, and can realize the desired objects. The present invention is based on these findings.

The modified PVA type polymers to be used according to the present invention are partially crosslinked synthetic polymers in the form of fine particles obtained by any of the several processes to be described later. The polymer particles absorb and hold fluids and swell to present the appearance of grapes in bunches and form hydrosol particles. Upon penetration of a fluid, the particles, whether they are dispersed like dots or like dense masses, immediately absorb the fluid and swell uniformly and evenly without losing the form of particles. Said hydrosol-like particles are substantially insoluble in water but come into contact with each other like grapes in bunches, whereas the fluid can freely pass through spaces among the particles and diffuses preferentially to surrounding particles still having a water absorbing power. Therefore, membranes or walls (unwetted lumps) are never formed in the boundary region between the portion composed of the hydrosol and the portion which is not yet a hydrosol. Since said hydrosol-forming particles have an intrinsically high water absorbing capacity, they still have an excellent wetting power even after absorption of fairly large amounts of water and relay with rapid diffusion the continuously incoming fluid to the neighboring particles so that the latter are wetted and as a result each particle reaches an equally wet state. Further, it is another feature of the particles that the fully swollen hydrosol particles can hold the excess incoming fluid within spaces among the individual particles. This feature is useful in greatly decreasing the surface wetting of such absorbent articles as diapers, sanitary napkins, sanitary tampons and blood absorbents for surgical operations and making the articles more comfortable to wear, as compared with the conventional articles.

It has been established that the hydrosol-forming particles to be used in the absorbent articles of the present invention, when once swollen and then evaporated to dryness at room temperature, can be restored approximately to the original forms, and that repetitions of such drying and water absorption do not cause any significant decrease in water absorbing capacity. Such a feature, which cannot be seen in any of the conventional absorbent materials, shows its marked effect in inhibiting the fluid once absorbed in a diaper, for instance, from being squeezed out under pressure as it is, for example, exerted by the human body.

The water absorbent materials of the invention can be obtained by reacting in anhydrous conditions a PVA type polymer in the form of a powder with a cyclic acid anhydride and thereby causing partial crosslinking of the polymer. The following six processes may be mentioned as useful for the preparation:

(1) Reacting in an anhydrous state a PVA type polymer in the form of a powder with a cyclic acid anhydride and causing thereby partial crosslinking simultaneously;

(2) Reacting in an anhydrous state a PVA type polymer in the form of a powder with a cyclic acid anhydride in the presence of a compound selected from the group consisting of hydroxides, alkoxides and salts of monovalent metals, tertiary amines and tertiary amine salts, whereby the polymer is partially crosslinked;

(3) Reacting in an anhydrous state a PVA type polymer in the form of a powder with a cyclic acid anhydride, thereby causing partial crosslinking, and then treating the polymer with a compound selected from the group consisting of hydroxides, alkoxides and salts of monovalent metals, ammonia, ammonium salts, amines and amine salts.

(4) Reacting in anhydrous state a PVA type polymer in the form of a powder with a cyclic acid anhydride, heating the resulting soluble, modified PVA type polymer to partially introduce crosslinkages, and thereafter treating the polymer with a compound selected from the group consisting of hydroxides, alkoxides and salts of monvalent metals, ammonia, ammonium salts, amines and amine salts;

(5) Reacting in an anhydrous state a PVA type polymer in the form of a powder with a cyclic acid anhydride in the presence of a compound selected from the group consisting of hydroxides, alkoxides and salts of monovalent metals, tertiary amines and tertiary amine salts, and heating the resulting soluble, modified PVA type polymer to partially introduce crosslinkages; or (6) Reacting in an anhydrous state a PVA type polymer in the form of a powder with a cyclic acid anhydride, then treating the polymer with a compound selected from the group consisting of hydroxides, alkoxides and salts of monovalent metals, ammonia, ammonium salts, amines and amine salts, and heating the resulting, soluble, modified PVA type polymer to cause partial crosslinking thereof.

The PVA type polymers that may be used as starting materials for making absorbent materials of the present invention include not only fully or partially saponified polymers and copolymers of vinyl acetate and various other vinyl esters, but also saponified copolymers of vinyl acetate and/or various other vinyl esters with a variety of unsaturated monomers such as alpha-olefins, vinyl chloride, acrylonitrile, acrylamide, acrylic esters and methacrylic esters, the content of said unsaturated comonomers being 30 mol % or less. Nevertheless, PVAs with molecular weights of 100–5000 and saponification degrees of 50–100 mol % are especially preferred.

The PVA type polymers to be subjected to the reaction preferably have the form of powders.

The cyclic acid anhydride to be used for the reaction is, for example, maleic, phthalic, succinic, glutaric, adipic and itaconic anhydride. Optionally, mixtures of these may be used. Especially suitable are maleic anhydride and phthalic anhydride.

The reaction is carried out in as an anhydrous a state as possible. Therefore, those compounds that have active hydrogen atoms reactive with the cyclic acid anhydride are unsuitable as solvents for the reaction, but those compounds that have no active hydrogen atoms, such as benzene, toluene, xylene, hexane, acetone, methylethyl ketone, tetrahydrofuran and dioxane, are used. Toluene and dioxane are especially suitable. When maleic anhydride is used for the reaction, this can also serve as a solvent because of its low melting point.

The reaction temperature to be employed in the reaction of the PVA type polymer with the cyclic acid anhydride is generally 30–150° C., and the reaction time is usually 30 minutes to 10 hours. Although the reaction proceeds almost quantitatively, the cyclic acid anhydride is used in excess as compared with the theoretical amount required to attain the desired degree of esterification.

The amount of the solvent is preferably 2–5 times the amount of the PVA type polymer powder.

The solid product is separated from the reaction mixture by filtration, centrifugation or some other method. The filtrate is recovered for reuse.

The solid product is washed with methanol, acetone or some other solvent, and dried, giving a modified PVA type polymer in the form of a powder.

In making the absorbent articles of the present invention by using as absorbent materials the modified PVA type polymer particles obtained by the above processes, generally, conventional absorbent materials, such as ground wood pulp, paper cotton, crepe paper, absorbent paper and fibrous sheet, in the form of multilayer structures or rolls are used as fluid absorbing holders or carriers, and the modified PVA type polymer particles are dispersed uniformly in the upper, middle and lower layer or in each of the compound layers resulting therefrom. The right side of the multilayer structure or roll is covered with a fluid permeable sheet and the back side is protected with a fluid impermeable film or the like, or both the right and back sides are covered with fluid permeable sheets so as to hold the absorbent material and form an aborbent body. In the case of a diapaer, for instance, considering the region where urination takes place and the amount of urine, it is most effective to disperse the modified PVA type polymer particles in the form of one or more layers in the upper and/or lower layer of the middle portion of the absorbent body. The right and back sides are then covered with holding sheets. In the case of blood absorbents for use in surgical operations, absorbent dressings for wounds, sanitary napkins, sanitary tampons and the like, these can be constituted in the same manner except that the kind of absorbent holders, the size and the thickness are altered in an appropriate manner.

This invention will be more fully described hereinbelow with reference to the accompanying drawings.

Figure 2:
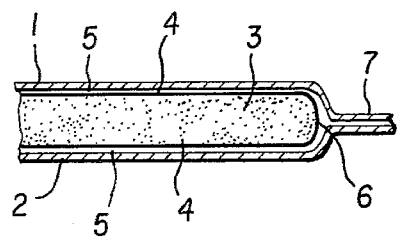
FIG. 2 is a cross-sectional view taken along line A—A of FIG. 1.

FIG. 1 is a perspective view of a diaper with a portion thereof cut off, wherein a right side surface sheet 1 is shown consisting of an absorbent, fluid-permeable, nonwoven fabric and having hollowed openings that are distributed in a zigzag manner. A back side surface sheet 2 is fluid impermeable and generally it is a polyethylene film. An absorbent pad 3 serves as a fluid absorbing holder and it is an elastic sheet full of cavities or pores and consisting of an accumulation of ground wood pulp, for instance. The modified PVA type polymer particles 4 are dispersed in the form of a uniform layer on the absorbent pad 3. The particle layer is covered by an absorbent, fluid-permeable, protective sheet 5, for exmple a sheet of tissue paper made from wood cellulose. Thus is formed a diaper absorbent body 6. At the time of pressing for forming the diaper absorbent body 6, the polymer particles 4 come into close contact with the absorbent pad 3 and are fixed thereby. FIG. 2 is a cross-sectional view taken along line A—A of FIG. 1. After covering the diaper absorbent body 6 with the right side sheet 1 and the back side sheet 2, the sheets are bonded together along the common edge 7 with an adhesive. The diaper is thus completed.

The dispersing of the modified PVA type polymer particles 4 is not limited to the upper or lower layer of the absorbent pad 3, but it is possible that an optional multilayer structure be disposed in one layer or in upper, middle and lower layers depending on the amount of fluids to be absorbed by the diaper. It is also possible to disperse them in the inner part of the pad 3 or to disperse or coat them within the protective sheet 5.

Figure 3:
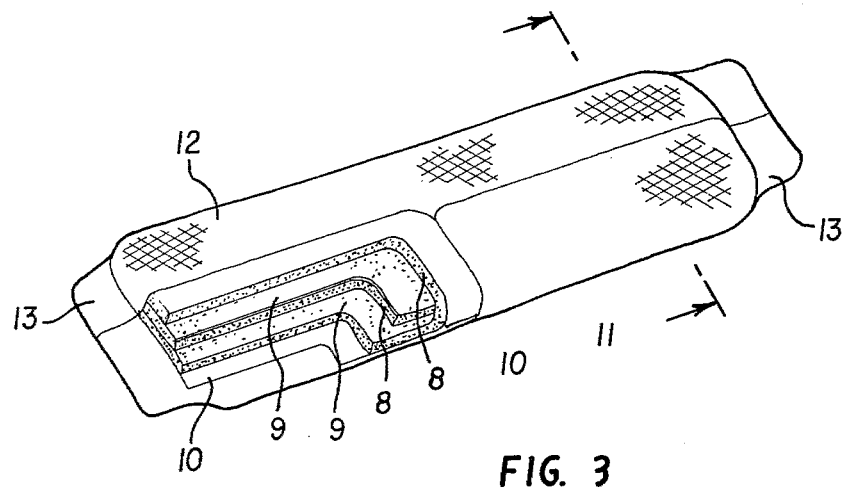
FIG. 3 is a perspective view of a sanitary napkin with a portion thereof cut off.
Figure 4:
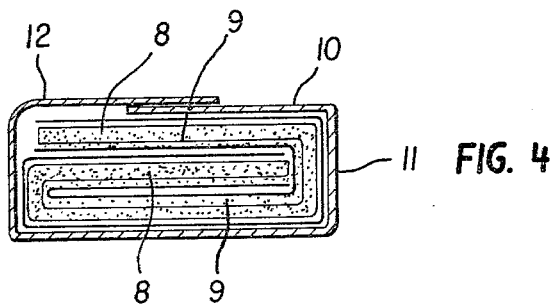
FIG. 4 is a cross-sectional view taken along line B—B of FIG. 3.

FIG. 3 is a perspective view of a sanitary napkin with a portion thereof cut off. A fluid absorbing holder 8 is shown on which the modified PVA type polymer particles 9 are dispersed in the form of a layer. The particle layer and the back side of the holder are each covered by a fluid permeable protective sheet 10 consisting for example of tissue paper. The whole unit is rolled in a cross-sectionally volute manner so that the fluid absorbing holder has a multilayer structure, and there is formed the absorbent body 11 of a sanitary napkin. FIG. 4 is a cross-sectional view taken along line B—B of FIG. 3, in which view it can be seen that the polymer particles 9 are interposed between the protective sheet 10 and thus fixed in the middle of the absorbent body 11 formed in the shape of a volute. The sanitary napkin absorbent body 11 is further covered all over the surface and at the same time held by a fluid permeable sheet 12. An edge 13 for prohibiting possible dislocation of the absorbent body 11, is generally fixed by embossing in a soft state without any adhesive agent. As the fluid absorbing holder 8, an absorbent pad consisting of an accumulation of ground wood pulp in the shape of a sheet or an absorbent entangled fiber sheet, for example, is used. As the fluid permeable sheet 12 there may be used a flexible nonwoven fabric sheet made from an absorbent fiber and having hollows or cavities disposed in a zigzag manner. The modified PVA type polymer particles 9 not only can be dispersed in the form of a layer in relation to the fluid absorbent holder 8, but also can be dispersed in the inner part thereof. It is also possible to disperse and fix them in the inside of the protective sheet 10.

Figure 5:
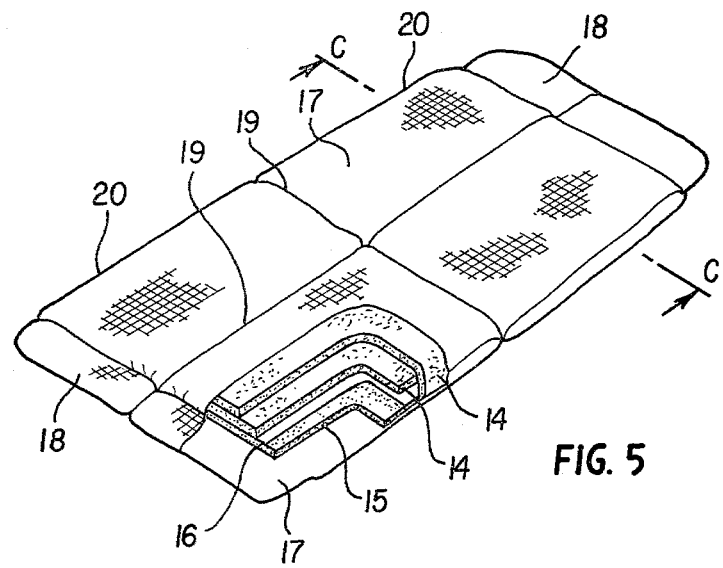
FIG. 5 is a perspective view of a blood absorbent for use in surgical operations, with a portion thereof cut off.
Figure 6:
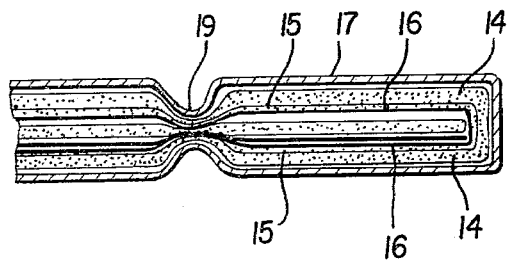
FIG. 6 is a cross-sectional view taken along line C—C of FIG. 5.

FIG. 5 is a persepective view of a blood absorbent for use in surgical operations with a portion thereof cut off. A fluid absorbing holder 14 is shown on the surface of which the modified PVA type polymer particles 15 are dispersed, forming a layer. The layer is covered by an absorbent, fluid-permeable protective sheet 16, such as a sheet of tissue paper, and the whole is rolled and then flattened to give a laminated body. The laminated body is covered or wrapped all over the surface with a fluid permeable packing sheet 17 so that possible leak from the absorbent material can be prevented, and the sheet portions overlapping at the edge portions 18 are firmly bonded together under pressure by using an adhesive. Furthermore, in order to prevent migration of the laminated body within the covering, embossing is done to provide the body with joining furrows 19. Thus is formed a blood absorbing body 20 for use in surgery. While the number of the migration-preventing, joining furrows 19 naturally can vary demanding upon the size of the absorbent body 20, it is preferable to provide them so that the unit area defined by the furrows may have dimensions between 2×3 cm and 10×20 cm. FIG. 6 is a cross-sectional view taken along line C—C of FIG. 5. As the fluid absorbing packing sheet 17, a flexible, microporous, water-absorbing nonwoven fabric or woven fabric, e.g. cotton crepe cloth having a wet strength may be used. In using the above blood absorbing body 20, by further coverin the surface thereof with a woven fabric having a good blood absoring power, such as for example cotton gauze, it is possible to promote absorption at minutely rugged or uneven sites.

Since the absorbent articles, such as diapers, in which the absorbent materials of the invention are used, contain as constituents those modified PVA type polymer particles, that have very high absorbency values, dispersed in and held by other fluid absorbing holders therefor, the articles can absorb large quantities of fluids but wet the surface only very little. Such a feature can never be found with the conventional articles. In particular, the same absorbency values can be attained by using the absorbency holders only in amounts of 50% by weight or less of the conventional ones, and therefore it is possible to reduce the volume of the absorbent articles by 30% or more. In this manner the present invention makes a great contribution to the concerned industries.

In addition to the aforementioned mode of making the absorbent bodies or articles which comprise dispersing the water absorbing materials obtained by the processes mentioned previously in relation to the production of the water absorbing materials in fluid absorbing holders therefor, it is also possible to employ another mode. This mode comprises dispersing in the fluid absorbing holder the modified PVA type polymer obtained by reacting in an anhydrous state a PVA type polymer with a cyclic acid anhydride, and at least one compound selected from the group consisting of salts of monovalent metals and ammonium salts, both in the form of powders, separately or in admixture, without reacting said modified polymer and said compound beforehand. In this case, said modified PVA type polymer and said salt, upon absorption of water, react with each other to form a salt, whereby water absorption is accelerated.

Having generally described this invention, further understanding can be obtained by reference to certain specific examples which are provided herein for purposes of illustration only and are not intended to be limiting unless otherwise specified.

EXAMPLE 1

A 500-cc separable three-necked flask was charged with 50 g of a powder-like PVA (polymerization degree: 1700 and saponification degree: 88 mol %), 30 g of maleic anhydride and 20.8 g of sodium hydrogen carbonate. Thereto were added 100 cc of dioxane and 100 cc of toluene as solvents, and the reaction was allowed to proceed with stirring at 80° C. for 4 hours. The reaction mixture was filtered off, and the solid matter was washed repeatedly with acetone, and dried. The product, a particulate modified PVA, weighed 100 g, and the modification degree (% increase in weight) calculated from the increase in weight was 100%.

This product was tested for water absorbing power. Thus, 1.000 g of the modified PVA particles accurately weighed was placed in a 500-cc beaker. Distilled water (500 g) in another beaker was transferred to the first beaker, stirred gently and then allowed to stand for 20 minutes, during which the modified PVA absorbed water and swelled and turned into hydrosol-like particles while the supernatant liquid became clear and transparent. The mixture was filtered on a filter paper over an hour at the end of which no filtrate dropped any longer. The filtrate was weighed, and the weight was subtracted from the weight of the distilled water previously poured into the beaker, i.e. 500 g. The so-calculated amount of water absorbed was divided by the weight of the modified PVA, i.e. 1.000 g to give an absorbency value of 150 g/g. Furthermore, the water held in the mass on the filter paper was partly squeezed out by using a previously wetted filter bag and by applying a load of 100 g/cm$^2$ over an hour. The amount of water squeezed out was weighed, and the absorbency calculated therefrom was 120 g/g.

EXAMPLE 2

Fifty grams (50 g) of a PVA with a polymerization degree of 1700 and a saponification degree of 99 mol %, 30 g of phthalic anhydrid,e, 2 g of triethylamine as catalyst for the reaction, and toluene as solvent were heated at 120° C. for 3 hours. The reaction mixture was filtered, and the solid matter was washed repeatedly with acetone and, after addition of 13.8 g of 25% aqueous ammonia, stirred in acetone at room temperature for 30 minutes. The reaction mixture was filtered, and the solid matter was washed repeatedly with acetone and dried, giving a particulate modified PVA.

This product was tested for water absorbing power by the procedure of Example 1. The absorbency calculated by weighing the filtrate after the filtration was 140 g/g and the water-holding capacity determined by weighing the water squeezed out under pressure was 120 g/g.

EXAMPLE 3

A diaper absorbent body 6, as mentioned previously referring to FIG. 1 and FIG. 2, was made by using as absorbing holder an absorbent pad 3 prepared from a sheet in which ground wood pulp was dispersed uniformly, cutting off therefrom a piece of a size 400×210 mm (weighing 15 g), dispersing on about two thirds of the surface exclusive of a pair of shorter opposite end portions on each side 2 g (4 g in all) of the modified PVA particles prepared in Example 1 so as to form a uniform layer, and covering each side with a sheet of tissue paper as protective sheet 5. This diaper absorbent body was covered by a flexible nonwoven rayon fabric having a size after cutting 460×330 mm and having hollows in a zigzag manner as right side surface sheet 1 and a polyethylene film cut to a size of 460×330 mm as back side sheet 2, then the edge portions 7 of the sheets were bonded together under pressure with an adhesive applied along the edge, and the whole was roller pressed evenly. There was prepared a diaper (specimen A) weighing 34 g (gross weight).

The diaper was subjected to a water absorption/diffusion test using a colored, simulated urine (97.09% distilled water, 1.94% urea, 0.80% sodium chloride, 0.11% magnesium sulfate heptahydrate and 0.06% calcium chloride). Thus, the diaper was placed in a horizontal position, and 60 cc of the colored, simulated urine was poured onto the middle point of the diaper and the diaper was then allowed to stand for 3 minutes. Then a high quality paper was applied onto the diaper, and the diaper roller pressed under a pressure of 100 g/cm$^2$ and dried at room temperature. After the driving, the area of the surface portion where coloration had occurred, i.e. where water absorption had taken place, each of the right side surface sheet, the right side and back side of the absorbent pad was measured. The results are shown in Table 1.

For comparison, three diapers, namely a diaper (specimen B) weighing 30 g and having the same constitution as that of specimen A except that it did not contain the modified PVA particles, a diaper (specimen C) weighing 40 g and having the same constitution as that of specimen A except that it did not contain the modified PVA particles and that a pad weighing 25 g was used as absorbing holder, and a commercially available diaper (specimen D) having outer dimensions 460×310 mm, weighing 50 g, containing an absorbing holder weighing 30 g and having essentially the same constitution as that of specimen B except that a flat sheet composed of an absorbing nonwoven fabric was used as right side surface sheet, were subjected to the water absorption/-diffusion test by the procedure mentioned above. The results are also shown in Table 1.

TABLE I

| Specimen (diaper) | Constitution | | | Colored area (cm²) | | |
|---|---|---|---|---|---|---|
| | Modified PVA (g) | Absorbing holder (g) | Weight of diaper (g) | holder Right side surface sheet | absorbing Right side | Back side |
| A | 4 | 15 | 34 | 97 | 157 | 178 |
| B | 0 | 15 | 30 | 171 | 251 | 344 |
| C | 0 | 25 | 40 | 117 | 145 | 260 |
| D | 0 | 30 | 50 | 153 | 379 | 431 |

As is clear from the above results, it was revealed that the diaper using the absorbent material of the present invention, when allowed to absorb the definite quantity of water, showed an excellent water absorbing performance as proven by those much smaller areas of the right side surface sheet and the absorbing holder that participated in water absorption than those measured with the other diapers. The smallness of said areas means a great latent absorbing capacity.

EXAMPLE 4

A diaper (specimen E) having a gross weight of 37.5 g and having the same constitution as that of specimen A, namely an absorbent article of the present invention made in Example 3, except that an absorbing pad composed of ground wood pulp dispersed uniformly in the shape of a sheet and weighing 18 g was used as absorbing holder.

The diaper was subjected to a water absorption test to be described below using distilled water and the simulated urine as used in Example 3. Thus, the diaper was placed in a horizontal position and distilled water or the simulated urine was poured onto the middle point of the diaper at a rate of 240 cc per minute. After allowing the diaper to absorb the aqueous fluid fully, the diaper was inclined for the excess test solution to drain. Then the wet diaper was weighed on druggists' scales, and the amount of water absorbed was calculated by subtracting the original weight from the weighing results. The results are shown in Table 2.

For comparison, a diaper (specimen F) weighing 33.5 g and having the same constitution as that of specimen E except that the modified PVA particles were not used, was subjected to the water absorption test by the procedure mentioned above. The results are also shown in Table 2.

TABLE 2

| Specimen (diaper) | Constitution | | Diaper weight (g) | Test solution | Fluid absorbed (g) |
|---|---|---|---|---|---|
| | Modified PVA (g) | Absorbing holder (g) | | | |
| E | 4 | 18 | 37.5 | Distilled water | 754 |
| E | 4 | 18 | 37.5 | Simulated urine | 460 |
| F | 0 | 18 | 33.5 | Distilled water | 293 |

It is evident from the above table that the absorbent article of the invention has a very great fluid absorbing capacity.

EXAMPLE 5

A 500-cc separable three-necked flask was charged with 50 g of a dried PVA in the powder form (polymerization degree: 1700, saponification degree: 88 mol %) and 30 g of maleic anhydride. Thereto were added 100 cc of dioxane and 100 cc of toluene as solvents, and the reaction was allowed to proceed with stirring at 80° C. for 5 hours. The reaction mixture was centrifuged, the solid matter washed twice with acetone, each time followed by centrifugation, and there was obtained about 100 g of a maleinized PVA powder containing about 20% by weight acetone.

To the modified PVA was added 100 cc or 200 cc of acetone, and the powder was dispersed therein with sufficient stirring.

To the dispersion system was added 237 cc of 1 N alkali methanol containing 16% water (the molar ratio of NaOH to the maleic anhydride used being 0.8), and stirring was continued for 10 minutes to cause neutralization of the carboxyl groups and sodium salt formation resulting therefrom.

The dispersion after the neutralization was centrifuged, the solid matter was washed with methanol and with acetone, each time followed by centrifugation, and then dried, to give about 76 g of a powdery resin in each case. The water absorption performance of each resin was as shown in Table 3, said performance varying depending on the amount of acetone added at the time of neutralization. The simulated urine used was of the same composition as that used in Example 3.

TABLE 3

| Polymer No. | Amount of acetone added at the time of neutralization (cc) | Absorbency (g/g) | |
|---|---|---|---|
| | | Deionized water | Simulated urine |
| 1 | 100 | 425 | 40 |
| 2 | 200 | 250 | 35 |

It can be seen from the results in Table 3 that there were obtained modified PVA resins with very excellent water absorption performance.

EXAMPLE 6

Following the procedure of Example 5 and using 50 g of the same PVA powder as in Example 5, 20 or 30 g of maleic anhydride, 100 cc of dioxane and 100 cc of toluene, the reaction was carried out with stirring at 80° C. for 4 hours. The reaction mixture was filtered, the solid matter washed twice with acetone, then dried and weighed. The maleinized PVA powder weighed 69 g (in the case of 20 g of maleic anhydride) and 78 g (in the case of 30 g of maleic anhydride), and these powders were blended with 17.2 g and 25.7 g, respectively, of sodium hydrogen carbonate.

The water absorption performance of each of the above resins is shown in Table 4. The simulated urine used had the same composition as that used in Example 3.

TABLE 4

| Polymer No. | Amount of maleic anhydride (g) | Amount of sodium hydrogen carbonate (g) | Absorbency (g/g) Deionized water | Absorbency (g/g) Simulated urine |
|---|---|---|---|---|
| 3 | 20 | 17.2 | 350 | 37 |
| 4 | 30 | 25.7 | 150 | 25 |

It can be seen from the results in Table 4 that there were obtained modified PVA resins with very excellent water absorption performance.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. An absorbent material for aqueous fluids comprising a modified polyvinyl alcohol polymer obtained by a process which consists essentially of reacting in an anhydrous organic diluent a partially or fully saponified polymer or copolymer of a vinyl ester in powder form with a cyclic acid anhydride; thereby causing partial crosslinking of said polymer.

2. The absorbent material of claim 1 wherein at least one compound selected from the group consisting of hydroxides, alkoxides and salts of monovalent metals, ammonia, ammonium salts, amines and amine salts, is reacted with said absorbent material during or after said partial cross linking.

3. The absorbent material of any of claims 1 or 3 wherein a polyvinyl alcohol having a polymerization degree of 100-5000 and a saponification degree of 50-100 mol % is used as said polyvinyl alcohol polymer.

4. The absorbent material of any of claims 1 or 3, wherein maleic anhydride or phthalic anhydride is used as said cyclic acid anhydride.

5. The absorbent material of any of claims 1 or 3 wherein the cross-linking of said polymer or copolymer is carried out in the presence of heat.

6. An absorbent body which comprises an absorbent material for aqueous fluids comprising a modified polyvinyl alcohol polymer obtained by a process which consists essentially of reacting in an anhydrous organic diluent a partially or fully saponified polymer or copolymer of a vinyl ester in powder form with a cyclic acid anhydride; thereby causing partial crosslinking of said polymer or copolymer; said absorbent material being dispersed in a fluid absorbing holder therefor.

7. The absorbent body of claim 6 wherein at least one compound selected from the group consisting of hydroxides, alkoxides, and salts of monovalent metals, ammonia, ammonium salts, amines and amine salts is reacted with said absorbent material during or after said partial cross linking.

8. The absorbent body of any of claims 6 or 7, wherein a polyvinyl alcohol having a polymerization degree of 100-5000 and a saponification degree of 50-100 mol % is used as said polyvinyl alcohol polymer.

9. The absorbent body of any of claims 6 or 7, wherein maleic anhydride or phthalic anhydride is used as said cyclic acid anhydride.

10. The absorbent body of claim 6 which is a diaper.

11. The absorbent body of claim 6 which is a sanitary napkin.

12. The absorbent body of claim 6 which is a sanitary tampon.

13. A method of absorbing fluids which comprises contacting said fluids with an absorbent material of claims 1 or 2.

* * * * *